United States Patent [19]

Spellmeyer et al.

[11] Patent Number: 5,536,853
[45] Date of Patent: Jul. 16, 1996

[54] OPIATE RECEPTOR LIGANDS

[75] Inventors: David C. Spellmeyer, Alameda; Walter H. Moos, Oakland; Eric J. Martin, El Cerrito; Ronald N. Zuckermann, Berkeley; Gregory Stauber, Danville; Kevin R. Shoemaker, San Francisco; Dane Goff, Redwood City, all of Calif.

[73] Assignee: Chiron Corporation, Emeryville, Calif.

[21] Appl. No.: 225,758

[22] Filed: Apr. 11, 1994

[51] Int. Cl.$^6$ .............. C07D 317/50; C07D 317/54; C07D 317/58; C07D 319/14
[52] U.S. Cl. .......... 549/441; 549/362; 549/434; 549/438; 549/439; 549/440; 549/445; 564/152; 564/153; 564/155; 564/158
[58] Field of Search .................. 514/456, 466, 514/616, 619, 621; 549/362, 438, 434, 439, 440, 441, 445; 564/152, 153, 155, 158

[56] References Cited

U.S. PATENT DOCUMENTS 5,272,175  12/1993  Hansen, Jr. et al. ............. 514/487

*Primary Examiner*—Ba Kim Trinh
*Attorney, Agent, or Firm*—Grant D. Green; Robert P. Blackburn

[57] ABSTRACT

Compounds of Formula 1 bind opioid receptors:

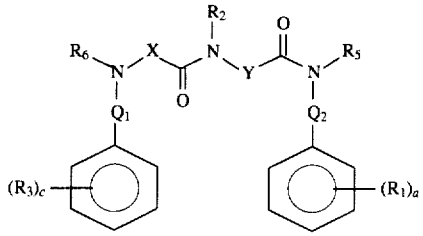

wherein X and Y are each independently

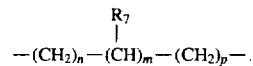

13 Claims, No Drawings

OPIATE RECEPTOR LIGANDS

DESCRIPTION

1. Technical Field

The invention relates generally to the field of medicinal chemistry, and specifically to compounds which bind to opioid receptors.

2. Background of the Invention

Opioid receptors are named for their binding affinity to morphine and other opium-derived compounds. The three classes of opioid receptor are designated p (morphine-like), κ(ketazocine-like), and δ.

Morphine:

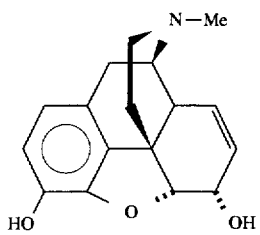

Ketazocine:

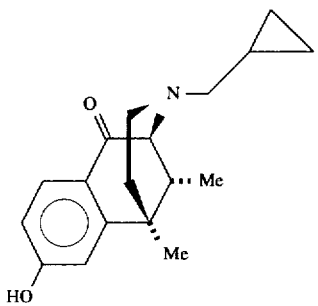

DISCLOSURE OF THE INVENTION

One aspect of the invention is a compound of Formula 1 which binds to the opioid receptor:

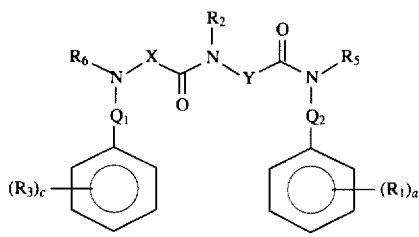

wherein X and Y are each independently

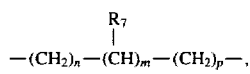

where n and p are each independently 0, 1, or 2; m is 1 or 2, and $R_7$ is H, lower alkyl, hydroxy-lower alkyl, phenyl, or aryl-lower alkyl;

$R_2$ is lower alkyl, alkenyl, haloalkyl, haloalkenyi, or

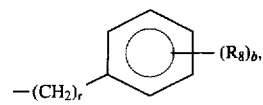

where r is an integer from 1 to 8 inclusive;

a, b, and c are each independently 1, 2, 3 or 4;

$Q_1$ and $Q_2$ are each independently

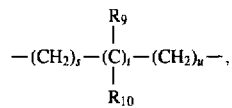

where s, t, and u are each independently 0 to 6 inclusive, and $R_9$ and $R_{10}$ are each independently H, OH, lower alkyl, hydroxy-lower alkyl, aryl, or

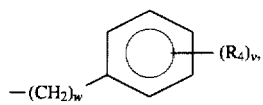

where v and w are each independently 0–4 inclusive;

$R_1$, $R_3$, $R_4$, $R_5$, $R_6$ and $R_8$ are each independently H, halo, OH, $NH_2$, $NO_2$, CN, SH, $SO_2$, $SO_3$, or —W—$(CH_2)_q$—Z–R, where q is an integer from 1 to 6 inclusive; R is H, lower alkyl, aryl, or benzyl, and W and Z are each independently a bond, —O—, —NR—, —S', —$SO_2$—, —$SO_3$—,

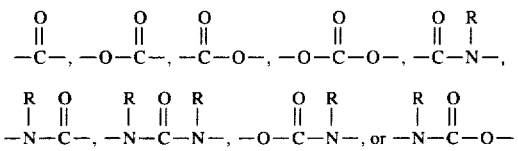

or two $R_1$, $R_3$, $R_4$ or $R_8$ together form a ring.

Another aspect of the invention is the method of modulating opioid receptor activity, comprising contacting an opioid receptor with a compound of formula 1.

Modes of Carrying Out The Invention

A. Definitions

The term "compound of formula 1" refers to compounds of the formula:

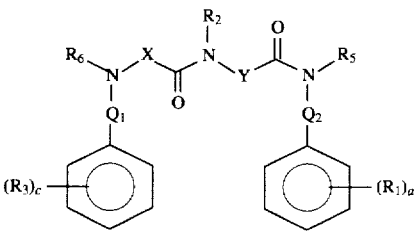

wherein X and Y are each independently

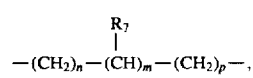

where n and p are each independently 0, 1, or 2; m is 1 or 2, and $R_7$ is H, lower alkyl, hydroxy-lower alkyl, phenyl, or aryl-lower alkyl;

R$_2$ is lower alkyl, alkenyl, haloalkyl, haloalkenyl, or

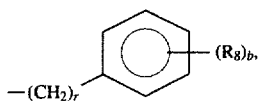

where r is an integer from 1 to 8 inclusive;

a, b, and c are each independently 1, 2, 3 or 4;

Q$_1$ and Q2 are each independently

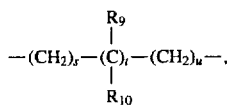

where s, t, and u are each independently 0 to 6 inclusive, and R$_9$ and R$_{10}$ are each independently H, OH, lower alkyl, hydroxy-lower alkyl, aryl, or

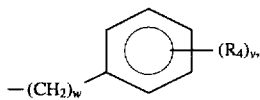

where v and w are each independently 0–4 inclusive;

R$_1$, R3, R$_4$, R$_5$, R$_6$ and R$_8$ are each independently H, halo, OH, NH$_2$, NO$_2$, CN, SH, SO$_2$, SO$_3$, or —W—(CH$_2$)$_q$—Z—R, where q is an integer from 1 to 6 inclusive; R is H, lower alkyl, aryl, or benzyl, and W and Z are each independently a bond, —O—, —NR—, —S—, —SO$_2$—, —SO$_3$—

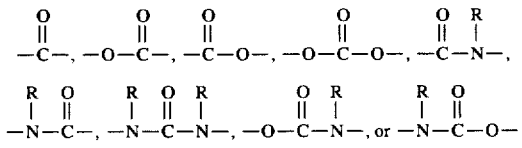

or two R$_1$, R$_3$, R$_4$ or R$_8$ together form a ring (for example, two R$_1$s may form an alkylenedioxy ring, such as

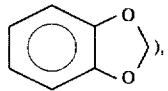

A presently preferred subgenus of compounds of formula 1 is that wherein X and Y are each —CH$_2$—, and R$_2$ is 3,4-methylenedioxybenzyl.

The term "peptoid" refers to monomers other than the twenty conventional amino acids and the common nucleotides and nucleosides (i.e., the DNA bases dA, dC, dG, and dT, and the RNA bases A, C, G, and U). The terms "amide peptoid" and nonconventional amino acid" refer to peptoids which are linked together through amide (peptide) bonds. Amide polypeptoid bonds may include substituents on the amide nitrogen atom. Presently preferred peptoids include those wherein the side chain (the residue attached to the backbone N) is selected from the following: 2-hydroxyethyl, 3-hydroxypropyl, 2-(4-hydroxyphenyl)ethyl, 2-phenethyl, 2,2-diphenylethyl, 1-naphthylmethyl, 4-(phenyl)phenyl, methyl, 2-methylpropyl, 2-methoxyethyl, pentyl, 1-ethylpropyl, cyclohexyl, (1-tetrahydrofuryl)methyl, 4-(phenoxy)phenyl, 3,4-methylenedioxybenzyl, 3,4-dimethoxybenzyl, 2-aminoethyl, 2-(N-morpholino)ethyl, 2-carboxyethyl, 2-(2-(2oaminoethoxy)ethoxy)ethyl, 2-methoxypyrid- 5-yl, adamantyl, 1-hydroxy-1-phenylprop-2-yl, 4oethenylphenyl, 4-biphenyl, 3-biphenyl, 4-butylphenyl, 4-cyclohexylphenyl, 4-iodophenyl, 2,2-diphenylethyl, 4-trifluoromethylbenzyl, 2-(4-chlorophenyl)ethyl, 2-(cyclohex-1-enyl)ethyl, 2-phenoxyethyl, 2-phenethylamino, 2-(4-sulfonamidophenyl-)ethyl, 3,4-dihydroxyphenethyl, 4-nitrophenethyl, 2-(4-hydroxyphenyl)-2-hydroxyethyl, 2-(4-aminophenyl)ethyl, and 6,7-dimethoxytetrahydroisoquinolinyl.

N-substituted glycine monomers are named Nxxx, where xxx is the multiletter abbreviation for the amino acid that has the corresponding side chain. An "h" immediately following the N indicates that the monomer is a homolog, having an additional —CH$_2$— between the nitrogen atom and the rest of the side chain (e.g., Nhhis has imidazolylethyl rather than imidazolyhnethyl as its side chain). An "m" following the N indicates an α-methyl residue (i.e., an N-substituted alanine instead of an N-substituted glycine): a "p" indicates an α-phenyl residue. A "p" following the N indicates that the backbone is β-alanine (3-aminopropanoic acid) rather than glycine. A "z" following the N indicates that the submonomer used is a hydrazine derivative, resulting in an N—N bond between the side chain and the backbone:

---

Nala = N-methylglycine (sarcosine);
Nglu = N-(2-carboxyethyl)glycine;
Nhhis = N-(imidazolylethyl)glycine;
Nlys = N-(4-aminobutyl)glycine;
Nmet = N-(2-methylthioethyl)glycine;
Nasn = N-(carbamylmethyl)glycine;
Nval = N-(1-methylethyl)glycine;
Nhtrp = N-(3-indolylethyl)glycine;
Nthr = N-(1-hydroxyethyl)glycine;
Norn = N-(3-aminopropyl)glycine;
Ncpro = N-cyclopropylglycine;
Nchex = N-cyclohexylglycine;
Ncoct = N-cyclooctylglycine;
Ncund = N-cycloundecylglycine;
Nbhm = N-(2,2-diphenylethyl)glycine;
Nbiph = N-(4-phenyl)phenylglycine;
Nmhphe = N-(2-phenethyl)alanine;
Nphtyr = N-(p-hydroxyphenethyl)beta-alanine;
Npbiph = N-(4-phenyl)phenylbeta-alanine;

Nasp = N-(carboxymethyl)glycine;
Nphe = N-benzylglycine;
Nile = N-(1-methylpropyl)glycine;
Nleu = N-(2-methylpropyl)glycine;
Nhser = N-(hydroxyethyl)glycine;
Ngln = N-(2-carbamylmethyl)glycine;
Narg = N-(3-guanidinopropyl)glycine;
Nhtyr = N-(p-hydroxyphenethyl)glycine;
Ncys = N-(thiomethyl)glycine;
Nhphe = N-(2-phenethyl)glycine;
Ncbut = N-cyclobutyglycine;
Nchep = N-cycloheptylglycine;
Ncdec = N-cyclodecylglycine;
Ncdod = N-cyclododecylglycine;
Nbhe = N-(3,3-diphenylpropyl)glycine;
Npop = N-(4-phenoxyphenyl)glycine;
Nphphe = N-(2-phenethyl)beta-alanine;

Nnbhm = N-(N-(2,2-diphenylethyl)carbamylmethyl)glycine;
Nnbhe = N-(N-(3,3-diphenylpropyl)carbamylmethyl)glycine;
Nbmc = 1-carboxy-1-(2,2-diphenylethylamino)cyclopropane;
Naeg = N-(2-aminoethyl)glycine;
Nzhphe = N-(2-phenethylamino)glycine
[or 2-phenethylhydrazopropanoic acid];
Nzhtyr = N-(p-hydroxyphenethylamino)glycine;
Noco = N-(3,4-methylenedioxyphenethyl)glycine;
Npen = N-pentylglycine;
Nddb = N-(3,4-dimethoxybenzyl)glycine;
Nedb = N-(3,4-ethylenedioxybenzyl)glycine;
Ntmb = N-(3,4,5-trimethoxybenzyl)glycine;
Nbha = N-(2,2-diphenylethyl)alanine;
Nvbhm = 4-(N-(2,2-diphenyl)ethyl)aminobut-2-enamide; and
Nbvp = N-(3,3-diphenylprop-2-enyl)glycine.

Nmdb = N-(3,4-methylenedioxybenzyl)glycine;

The term "alkyl" as used herein refers to saturated hydrocarbon radicals containing from 1 to 30 carbon atoms, inclusive. Alkyl radicals may be straight, branched, or cyclic. Exemplary alkyl radicals include n-pentyl, n-hexyl, n-octyl, n-dodecyl, 2-dodecyl, 4-octadecyl, 3,5-diethylcyclohexyl, duryl, and the like. The term "lower alkyl" as used herein refers to straight, branched, and cyclic chain hydrocarbon radicals having from 1 to 8 carbon atoms, such as methyl, ethyl, propyl, isopropyl, n-butyl, s-butyl, t-butyl, n-pentyl, n-hexyl, cyclopentyl, cyclohexyl, 2-methylcyclopentyl, cyclopentylacetyl, and the like. "Alkoxy" refers to radicals of the formula —OR, where R is alkyl as defined above: "lower alkoxy" refers to alkoxy radicals wherein R is lower alkyl. "Hydroxy-lower alkyl" refers to radicals of the formula HO—R—, where R is lower alkylene of 1 to 8 carbons, and may be straight, branched, or cyclic. "Hydroxy-lower alkoxy" refers to radicals of the formula HO—R—O—, where R is lower alkylene of 1 to 8 carbons, and may be straight, branched, or cyclic. "Lower alkoxy-lower alkyl" refers to groups of the formula $R_aO—R_b—$, where $R_a$ and $R_b$ are each independently lower alkyl. "Lower alkoxy-lower alkoxy" refers to groups of the formula $R_aO—R_bO—$, where $R_a$ and $R_b$ are each independently lower alkyl.

"Alkenyl" refers to hydrocarbon radicals of 2–20 carbon atoms having one or more double bonds. Alkenyl radicals may be straight, branched, or cyclic. Exemplary alkenyl radicals include 1-pentenyl, 3-hexenyl, 1,4-octadienyl, 3,5-diethylcyclohexenyl, and the like. "Lower alkenyl" refers to alkenyl radicals having 2–8 carbon atoms.

The term "alkynyl" refers to hydrocarbon radicals of 2–20 carbon atoms having one or more triple bonds. Alkynyl radicals may be straight, branched, or cyclic. Exemplary alkynyl radicals include 1-pentynyl, 3-hexynyl, octa-2-yn-6-enyl, 3,5-diethylcyclohexynyl, and the like. "Lower alkynyl" refers to alkynyl radicals having 2–8 carbon atoms.

The term "haloalkyl" refers to an alkyl radical substituted with one or more halogen atoms. Exemplary haloalkyl radicals include trifluoromethyl, 2,2,2-trifluoroethyl, -chlorocyclohexyl, 2-bromo-3-chlorocyclohexyl, 2,3-dibromobutyl, and the like.

The term "haloalkenyl" refers to an alkenyl radical substituted with one or more halogen atoms. Exemplary haloalkenyl radicals include 3-chloroprop-2-enyl, 4,4-dichlorobut- 2-enyl, 5-bromo-3-methylcyclohex-2-enyl, and the like.

"Aryl" refers to aromatic hydrocarbons having up to 14 carbon atoms, preferably phenyl or naphthyl. "Aryl-lower alkyl" refers to radicals of the form Ar—R—, where Ar is aryl and R is lower alkyl. "Aryloxy" refers to radicals of the form Ar—O—, where Ar is aryl. "Aryloxy-lower alkyl" refers to radicals of the form ArO—R—, where Ar is aryl and R is lower alkyl.

The term "acyl" refers to a radical of the formula RCO—, in which R is H, alkyl as defined above, phenyl, benzyl or naphthyl. Exemplary acyl groups include acetyl, propionyl, formyl, t-butoxycarbonyl, benzoyl, and the like. "Lower acyl" refers to radicals wherein R is lower alkyl.

The term "halo" refers to a halogen radical, such as F, Cl, Br, or I.

The term "treatment" as used herein refers to reducing or alleviating symptoms in a subject, preventing symptoms from worsening or progressing, inhibition or elimination of the causative agent, or prevention of the infection or disorder in a subject who is free therefrom. Thus, for example, treatment of opiate addiction in a patient may be reduction of opiate effect (blockade), or the prevention of relapse in a patient who has been cured.

The term "preparation" refers to a sample to be tested for the presence of opioid receptor. Preparations may be whole tissues, tissue homogenates, host cells (e.g., recombinant host cells), biopsy samples, blood and/or blood fractions, lymph, and the like.

B. General Method

Compounds of the invention are easily synthesized by standard chemical methods. The presently-preferred method of synthesis is the "submonomer" technique described by R. Zuckermann et al., *J Am Chem Soc* (1992) 114:10646–7, incorporated herein by reference. Briefly, an activated solid-phase synthesis resin is treated to remove any protecting or capping groups, then acylated with an acetic acid derivative having a good leaving group (e.g., bromoacetic acid) under standard conditions. The leaving group is then displaced in an $S_N2$ displacement reaction using an amine corresponding to the desired side chain, producing a secondary amine. The resulting secondary amine is then acylated with an acetic acid derivative, and the cycle repeated for each desired sidechain. Compounds in which $R_7$ is a residue other than H are synthesized by employing an acetic acid derivative incorporating the desired residue. Thus, where $R_7$ is methyl one would employ 2-bromopropanoic acid.

For example, to synthesize the compound Nhtyr-Nbiph-Nhphe, the acylated resin is treated with phenethylamine (to provide the homo-Phe side chain), acylated with bromoacetic acid, the bromine displaced with 4-aminobiphenyl (to provide the 4-(phenyl)phenyl side chain), acylated with bromoacetic acid, and the bromine displaced with 4-hydroxyphenethylamine (to provide the homo-Tyr side chain). The last amine may be further acylated or alkylated to reduce the basicity of the compound. The compound is then cleaved from the resin using standard methods, providing either an acid or an amide, depending upon the cleavage conditions.

In either case, the terminal carbonyl function may be converted to an amide, acid, aldehyde, alcohol, amine or other group as desired. The final compound is typically purified by chromatography. If desired, simple acid addition salts and/or esters may be prepared using standard techniques.

Compounds of the invention may also be prepared by traditional solution-phase synthesis, beginning with an ester of bromoacetic acid, and proceeding as described above. Alternatively, one may synthesize compounds in the N→C direction in the solution phase, using complete monomers (rather than "submonomers"). For example, Fmoc-protected Nhtyr (with Fmoc protecting the amine) may be condensed with Nbiph-tBu ester with N,N-diisopropylcarbodiimide (DIC) in DIEA/$CH_2Cl_2$ to forIn (Fmoc)Nhtyr-Nbiph-tBu. The tBu ester is then removed with trifluoroacetic acid (TFA) and scavengers, and the compound condensed with Nhtyr-tBu ester to form (Fmoc)Nhtyr-Nbiph-Nhtyr-tBu. The compound is then deprotected using TFA, scavengers, and pyrrolidine to provide Nhtyr-Nbiph-Nhtyr. Alternatively, one may use tBOC-protected Nhtyr, and employ methyl esters of Nbiph and Nhtyr, cleaving the esters with NaOH rather than TFA with scavengers. It may be necessary to isolate intermediate stage compounds, e.g., by chromatography or fractional crystallization.

The reactants employed in synthesis of the compounds are generally commercially available. Other reactants (e.g., less-common substituted amines) may be prepared by standard chemical means from amines that are commercially available.

Compounds of the invention may be assayed for activity using standard protocols. For example, one may employ the protocol demonstrated in the Examples below to determine binding of compounds of the invention to any desired receptor subtype (e.g., using different sources of tissue). Compounds which exhibit strong binding to receptors will exert either agonistic or (more usually) antagonistic activity, which may be determined by means of appropriate tissue-based or in vivo assays known in the art. Compounds within the scope of the invention may easily be assayed for activity by standard receptor-binding assays.

The compounds of the invention may be administered by a variety of methods, such as intravenously, orally, intramuscularly, intraperitoneally, bronchially, intranasally, and so forth. The preferred route of administration will depend upon the nature of the compound and the condition to be treated. Compounds may be administered orally if well absorbed and not substantially degraded upon ingestion (compounds of the invention are generally resistant to proteases). The compounds may be administered as pharmaceutical compositions in combination with a pharmaceutically acceptable excipient. Such compositions may be aqueous solutions, emulsions, creams, ointments, suspensions, gels, liposomal suspensions, and the like. Thus, suitable excipients include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol®, vegetable oils, and the like. One may additionally include suitable preservatives, stabilizers, antioxidants, antimicrobials, and buffering agents, for example, BHA, BHT, citric acid, ascorbic acid, tetracycline, and the like. Cream or ointment bases useful in formulation include lanolin, Silvadene® (Marion), Aquaphor® (Duke Laboratories), and the like. Other topical formulations include aerosols, bandages, sustainedrelease patches, and the like. Alternatively, one may incorporate or encapsulate the compound in a suitable polymer matrix or membrane, thus providing a sustained-release delivery device suitable for implantation near the site to be treated locally. Other devices include indwelling catheters and devices such as the Alzet® minipump. Further, one may provide the compound in solid form, especially as a lyophilized powder. Lyophilized formulations typically contain stabilizing and bulking agents, for example human serum albumin, sucrose, mannitol, and the like. A thorough discussion of pharmaceutically acceptable excipients is available in *Remington's Pharmaceutical Sciences* (Mack Pub. Co.).

Compounds of the invention may be used to detect the presence of opiate receptor in tissues, cells, body fluids, and the like, exploiting the fact that compounds of the invention bind to opiate receptor. In general, a sample is obtained, and is contacted with a compound of the invention under physiological conditions. The sample is then rinsed, and examined for binding of the compound. Examination may be facilitated by using labeled compound (e.g., radiolabeled with $^3H$, $^{13}C$, $^{125}I$, and the like). This assay may be useful, inter alia, for examining expression of opiate receptor in recombinant host cells, and for studying pathological distributions of opiate receptor.

C. Examples

The examples presented below are provided as a further guide to the practitioner of ordinary skill in the art, and are not to be construed as limiting the invention in any way.

EXAMPLE 1

(Preparation of Compounds)

Compounds of the invention are prepared as follows:

A.) General Synthesis of Compounds

Oligomer synthesis was performed on a Rink amide polystyrene resin (0.61 mmol/g, 1% crosslinked, 100–200 mesh). N,N-Dimethylformamide (DMF), dimethylsulfoxide (DMSO), methylene chloride, glacial acetic acid and trifluoroacetic acid (TFA) were obtained from commercial suppliers and used without further purification. Piperidine, bromoacetic acid, N,N-diisopropylcarbodiimide (DIC), 4-aminobiphenyl, tyramine, 3,4-methylenedioxybenzylamine, 2,2-diphenethylamine, and other reagents were obtained from Aldrich and used without further purification.

All reactions were performed at room temperature in a 2.0 L vessel equipped with a 10 cm coarse glass frit. Agitation of the resin-reagent slurry was performed at every step by rotary shaking at 200 rpm. Filtration of the resin-reagent slurry was achieved by the application of vacuum.

A 2.0 L vessel was charged with Rink amide resin (100 g, 0.061 mol). The resin was briefly swelled in DMF (1.5 L) with gentle agitation and drained. The 9-fluorenyhnethoxycarbonyl (Fmoc) group was then removed by treatment with 20% piperidine/DMF (1.7 L, 1×5 rain, followed by 1×20 rain). The resin was then washed with DMF (6×1.7 L). The remainder of the compound was synthesized by performing three cycles of acylation with bromoacetic acid and displacement with an amine.

General acylation conditions (0.061 mol resin)

Resin-bound amines were bromoacetylated by in situ activation with DIC. To the oligomer-resin was added a DMF solution of bromoacetic acid (0.67 M, 900 mL) followed by DIC (neat, 93 mL, 0.60 tool). The reaction mixture was agitated for 30 min at room temperature. The mixture was drained and the reaction was repeated once. The resin was washed with DMF (3×1.7 L).

General displacement conditions (0.61 mol)

Resin-bound bromoacetamides were displaced by the addition of the amine as a solution in DMSO (1–2 M, 1.0 L). The reaction mixture was agitated at room temperature for 2 hours. The reaction mixture was drained and the resin was washed with DMF (3×1.7 L). Reagents were used at 2.0 M concentration, except tyramine and. phenethylhydrazine (used at 1.0 M).

General Cleavage and Purification

After completion of the synthesis the resin was washed with $CH_2Cl_2$ (3×1.7 L) and air-dried for 5 minutes. The full length trimer was cleaved from the resin (0.061 mol) by treatment with 95% TFA/5% water (1.5 L) at room temperature for 15 minutes. The resin was then washed with 95% TFA/5% water (1×1.0 L) and $CH_2Cl_2$ (1 ×1 L). The filtrates were pooled and the solvent removed by rotary evaporation. The residue was dissolved in glacial acetic acid (150 mL) and lyophilized.

B.) Synthesis of Nbhm-Nmdb-Nhtyr (CHIR-4531)

The compound Nbhm-Nmdb-Nhtyr (Nbhm=N-benzhydryhnethylglycine; Nmdb=N-(3,4-methylenedioxybenzyl)glycine; and Nhtyr=N-4-hydroxyphenethylglycine) was synthesized as described in part A) above, using 4-hydroxyphenethylamine as the first amine added, 3,4-methylenedioxybenzylamine as the second amine added, and benzhydryhnethylamine as the third amine added.

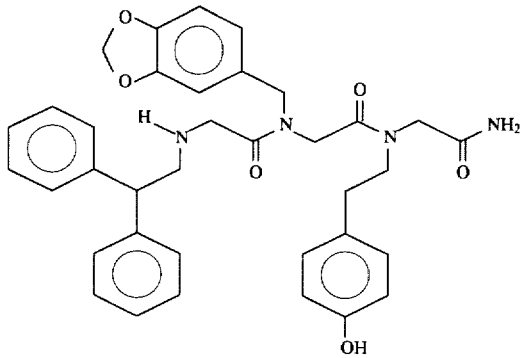

After completion of the synthesis the resin was washed with $CH_2Cl_2$ (3×1.7 L) and air dried for 5 minutes. The full length trimer was cleaved from the resin (0.061 mol) by treatment with 95% TFA/5% water (1.5 L) at room temperature for 15 minutes. The resin was then washed with 95% TFA/5% water (1×1.0 L) and $CH_2Cl_2$ (1 ×1 L). The filtrates were pooled and the solvent removed by rotary evaporation. The residue was dissolved in glacial acetic acid (150 mL) and lyophilized to afford the crude product (CHIR4531, depicted above). The purity of the crude product was determined by reverse-phase HPLC. The product was characterized by FAB-mass spectrometry.

C.) Synthesis of Backbone Variants

Proceeding as described in part A) above, but substituting 3-bromopropanoic acid, 2-bromopropanoic acid, and 2-phenyl-3-bromopropanoic acid for bromoacetic acid at some positions, compounds wherein X and/or Y are other than —$CH_2$— are prepared.

D.) Synthesis of Additional Compounds

Other compounds are prepared proceeding as in part A above, but substituting for 2,2-diphenethylamine the following compounds: 2,2-diphenylpropylamine, 3,3-diphenylpropylamine, tritylamine, benzhydrylamine, 2-phenethylamine, 2-phenethylhydrazine; 2-hydroxy-2,2-diphenethylamine, 2-(4-t-butyl)phenethylamine, 2-phenylpropylamine, 2-(4-methyl)phenethylamine, 2-(4-ethyl)phenethylamine, (naphth-1-yl)(phenyl)methylamine, (4-methylphenyl)(phenyl)methylamine, (4-chlorophenyl)(phenyl)methylamine, 2-(2-chlorophenyl)ethylamine, 1-phenyl-2-methylprop-2-ylamine, 1-phenyl-prop-2-ylamine, 2-(4-chlorophenyl)ethylamine, 2-(3-chlorophenyl)ethylamine, 2-(3-fluorophenyl)ethylamine, and 1-(4-chlorophenyl)-2-methylprop-2-ylamine.

The following reactants are substituted for 3,4-methylenedioxybenzylamine: 3,4-methylenedioxybenzhydrazide, 3,4-methylenedioxyphenethylamine, 3,4-methylenedioxybenzylthiosemicarbazide, 1-(3,4-methylenedioxyphenyl)prop-2-ylamine, veratrylamine, 3,4-methylenedioxyaniline, 6-amino-3,4-methylenedioxyacetophenone, 1,2-dimnino-4,5-methylenedioxybenzene, 3-methyoxy-4-hydroxybenzylamine, 6,7-methylenedioxynaphthylamine, 3-methyoxy-2-hydroxybenzylamine, 2,3-dimethoxybenzylamine, 3,4,5-trimethoxybenzylamine, 4-methoxybenzhydrylamine, 2,4-dimethoxybenzylamine, 2,4,6-trimethoxybenzylamine, 2-ethoxybenzylamine, 1-(3,4-dimethoxyphenyl)-2-phenethylamine, 4-(4-methoxyphenyl)phenylamine, 2-(3-chlorophenoxy)ethylamine, 2-amino-4,5-dimethoxybenzamide, 3-methoxyphenethylamine, 4-amino-2-methylnaphthol, 3-hydroxybenzylhydrazine, lauryamine, decylamine, nonylamine, octylamine, 1,12-diaminododecane, 1,10-diaminododecane, 1,9-diaminododecane, 1,8-diaminododecane, 1,1,3,3-tetramethylbutylamine, 2-amino- 3-methylbutane, 2-octylamine, isobutylamine, 1,3-diaminopropane, 1,1-dimethylpropylamine, 1,4-dimethylheptylamine, 2,2-dimethylpropylamine, 1,2-diaminopropane, 2-aminopropane, pentylamine, 1,5-diaminopentane, 1,5-diamino-2-methylpentane, 2-aminohexane, hexylamine, 2-aminopentane, butylamine, 2-amino-5-methylhexane, 3-aminoheptane, 1,6-hexanediamine, 1,3-dimethylbutylamine, 4-methylbutylamine, 2-methylbutylamine, 1-ethylpropylamine, 1,4-diaminobutane, 2-ethylhexylamine, 2-aminoheptane, heptylamine, 1,7-diaminoheptane, 3-amino-2,4-dimethylpentane, 1,2-diaminobutane, 2-aminobutane, propylamine, 1,5-dimethylhexylamine, 1,6-diamino-2,4,4-trimethylhexane, stearylamine, pahnitylamine, pentadecylamine, tetradecylamine, and tridecylamine.

The following reactants are substituted for tyramine: phenethylamine, benzylamine, 3,4-methylenedioxyphenethylamine, 3-tfifluoromethylphenethylamine, 2-chlorophenethylamine, 3-chlorophenethylamine, phenylpropylamine, 4-chlorophenethylamine, 2,4-dichlorophenethylamine, 3-bromophenethylamine, 4-iodophenethylamine, 3-hydroxyphenethylamine, 4-hydroxyphenethylamine, 2,4-dihydroxyphenethylamine, 2-methylphenethylamine, 3-methylphenethylamine, 4-methylphenethylamine, 2,4-dimethylphenethylamine, 2,4,6-trimethylphenethylamine, 3-ethylphenethylamine, 4-ethylphenethylamine, 4-hexylphenethylamine, 3-nitrophenethylamine, 2-aminophenethylamine, 4-aminophenethylamine, 2,4-diaminophenethylamine, 2-methoxyphenethylamine, 3-methoxyphenethylamine, 4-methoxyphenethylamine, 2,4-dimethoxyphenethylamine, 2,4,6-trimethoxyphenethylamine, 3,4-dimethoxyphenethylamine, 2-ethoxyphenethylamine, 3-ethoxyphenethylamine, 4-ethoxyphenethylamine, 3-propoxyphenethylamine, 4-butoxyphenethylamine, 4-t-butoxyphenethylamine, 3-methoxymethylphenethylamine, 4-methoxymethylphenethylamine, 3-(2-methoxyethyl)phenethylamine, 4-(2-methoxyethyl)phenethylamine, 4-(2hydroxyethyl)phenethylamine, 4-(3-hydroxypropyl)phenethylamine, 4-(2-hydroxyethoxy)phenethylamine, 4-phenylphenethylamine, 4-(2-chlorophenyl)phenethylamine, 4-(2-aminophenyl)phenethylamine, 3-(2,4,6-trimethylphenyl)phenethylamine, 4-phenoxyphenethylamine, 4-(3-chlorophenoxy)phenethylamine, 4-(4-aminophenoxy)phenethylamine, 3-benzylphenethylamine, 4-phenethylphenethylamine, 3-acetylphenethylamine, 4-acetylphenethylamine, 4-(2-phenoxyethyl)phenethylamine, and 3-benzyloxyphenethylamine.

The compounds corresponding to the above-listed substitutions are prepared following the procedure set forth in part A) above.

EXAMPLE 2

(Activity In Vitro)

Compounds were screened in vitro using the following assay:

High-affinity ligands for the μ-specific opiate receptor were identified from a diverse peptoid library by testing the pools of compounds in solution-phase radioligand competition assays, and tracing the binding activity to individual compounds by iterative resynthesis and screening of smaller sub-pools.

Rat forebrains were homogenized and washed in 50 mM Tris, pH 7.5 containing 20 mM NaCl, 5 mM EGTA, 2 mM $MgCl_2$, 21 μg/mL aprotinin, 0.5 mg/L leupeptin, 0.7 mg/L pepstatin, 0.2 Mm PMSF. 50 μL of membrane (10 mg/mL protein) were dispensed into 1 mL of 50 mM Tris, pH 7.5, 1 nM [$^3$H]-DAMGO and the peptoid mixture. All assays were performed at 100 nM per peptoid.

Nonspecific binding was determined as [$^3$H]-DAMGO bound in the presence of 1 μM naloxone. Incubation was for 1 hr at room temperature. Unbound radioactivity was removed by rinsing the membranes on Whatman GF/B glass fiber filters. Each filter was washed 3 times with 3 mL of 50 mM Tris, pH 7.5, 4° C. Filters were soaked overnight in 5 mL of Beckman ReadySafe scintillation cocktail and then counted for one minute in a Wallac 1409 liquid scintillation counter. Assays were performed in duplicate.

Compound CHIR-4531 (Nbhm-Nmdb-Nhtyr) exhibited a $K_i=7$ nM. Compound CHIR-4534 (Nbhm-Npen-Nhtyr) exhibited a $K_i=30$ nM. Compound CHIR-4537 (Nbhm-Nddb-Nhtyr) exhibited a $K_i=45$ nM.

| CHIR | Compound | $K_i$ | % Inhibition at 100 nM |
|---|---|---|---|
| 4531 | Nbhm-Nmdb-Nhtyr | 7 nM | |
| 4534 | Nbhm-Npen-Nhtyr | 30 nM | |
| 4537 | Nbhm-Nddb-Nhtyr | 45 nM | |
| 4622 | Nbhe-Nmdb-Nhtyr | | 78% |
| 4626 | Nbhm-Ntrnb-Nhtyr | | 86% |
| 4627 | Nbhm-Nphe-Nhtyr | | 90% |
| 4628 | Nbhm-Nphe-Nhphe | | 77% |
| 5052 | Nbha-Nmdb-Nhtyr | | 73% |
| 5045 | Nvbhm-Nmdb-Nhtyr | | 58% |
| 5062 | Nbvp-Nmdb-Nhtyr | | 65% |

EXAMPLE 3

(Assay In vivo)

Compounds of the invention are tested in vivo as follows: Male Swiss (ICR) mice (25–30 g) and male Sprague Dawley albino rats (100–125 g) are housed in groups of 5, and allowed food and water ad libitum until the beginning of the experiment.

A. Mouse stretch test: This procedure is a general, non-specific test for detecting antinociceptive activity in a wide variety of pharmacological agents. Each mouse (n=10) is administered either vehicle or test compound (0.1 mg/Kg to 300 mg/Kg) subcutaneously. After 5 rain, dilute acetic acid (0.6%) is injected i.p. (0.25 mL/25 g). Each animal is then observed after an additional 5 min, and the number of abdominal twists/hind leg stretches displayed by each mouse is counted for a 5 min. test period. Percent inhibition of response is calculated from 100×(mean number of stretches in vehicle group - mean number of stretches per mouse)/(mean number of stretches in vehicle group). The dose of compound causing 50% antinociception (at 95% confidence limits) is calculated by regression analysis.

Oral studies are performed with different mice. Test compound (or vehicle) is administered orally, followed by acetic acid injection 25–55 min after administration.

Antagonism studies are performed by first obtaining a dose-response crowe for s.c. morphine and vehicle. Mice are administered test compound s.c., (0.1 mg/Kg to 300 mg/Kg) followed 5 rain later by morphine in one of 4 doses s.c. (determined according to standard experimental protocol). Morphine antagonism is demonstrated if the morphine dose-response curve is displaced to the right.

B. Rat Formalin Test: Dilute formalin provides a continuous (tonic) background of pain that may be neurochemically and neurophysiologically different from the transient (phasic) pain associated with hot plate and tail-flick tests.

Rats (n=8) are acclimated to individual Plexiglas observation chambers for at least 1 hr prior to testing. Each animal is then injected with 5% formalin (50 μL) or saline (50 μL) s.c. into the dorsal surface of the right hind paw. The rats display two spontaneous behaviors indicative of pain: flinching/shaking of the paw and/or hindquarters, and licking or biting of the injected paw. Flinching is the most reliable behavior to score in rats. The behavior is monitored between 0–10 rain (early/acute phase) and 20–35 min (late/tonic phase) following injection.

Four doses of test compound are injected s.c. (0.1 mg/Kg to 300 mg/Kg). The pretreatment time is chosen so that peak antinociceptive activity coincides with the late/tonic phase of response. Results are expressed as mean % antagonism of formalin-induced flinching, and are calculated for individual, drug-treated formalin-injected rats.

C. Neuroadaptation of Rats: This protocol provides information on how rats react to multiple doses of test compounds, and on eventual challenge with naloxone, a standard antagonist of opioid receptors.

Four groups of 6 rats are injected s.c. with either vehicle or test compound at 8:00 AM, 4:00 PM, and midnight over 5 days. On the fifth day, only the morning injection is administered. The initial dosages are: day 1=1 mg/Kg, day 2=2 mg/Kg, days 3–5=4 mg/Kg. Naloxone (3 mg/Kg, s.c.) or saline is administered 4 hr after the final injection of test compound.

On day 4, the rats are acclimated to Plexiglas observation cages in a constant temperature room (20° C.). The animals are trained to have their weights and rectal temperature taken. On day 5, this procedure is repeated before noting baseline readings, and challenging with naloxone or saline. Behaviors are monitored for 30 min before and after challenge with naloxone or saline. After the final weighing and temperature reading, 1 hr post challenge, each animal is euthanized with solid $CO_2$.

Behavioral changes in the 4 groups of rats (vehicle-saline, vehicle-naloxone, compound-naloxone, compound-saline) are assessed by a point-scoring technique (with weighted signs): Cowan et al., *J Pharmacol Exp Ther* (1988) 246:950.

What is claimed:

1. A compound of Formula 1:

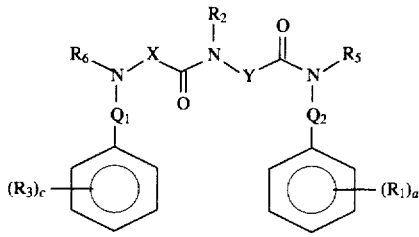

wherein X and Y are each independently

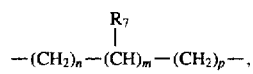

where n and p are each independently 0, 1, or 2; m is 1 or 2, and $R_7$ is H, lower alkyl, hydroxy-lower alkyl, phenyl, or aryl-lower alkyl;

$R_2$ is lower alkyl, alkenyl, haloalkyl, haloalkenyl, or

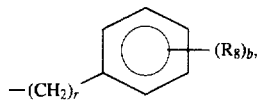

where r is an integer from 1 to 8 inclusive;
a, b, and c are each independently 1, 2, 3 or 4;
$Q_1$ and $Q_2$ are each independently

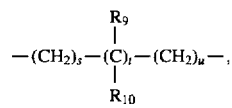

where s, t, and u are each independently 0 to 6 inclusive, and $R_9$ and $R_{10}$ are each independently H, OH, lower alkyl, hydroxy-lower alkyl, aryl, or

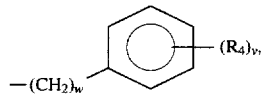

where v and w are each independently 0–4 inclusive;
$R_1$, $R_3$, $R_4$, $R_5$, $R_6$ and $R_8$ are each independently H, halo, OH, $NH_2$, $NO_2$, CN, SH, $SO_2$, $SO_3$, or —W—$(CH_2)_q$—Z—R, where q is an integer from 1 to 6 inclusive; R is H, lower alkyl, aryl, or benzyl, and W and Z are each independently a bond, —O—, —NR—, —S—, —$SO_2$—, —$SO_3$—,

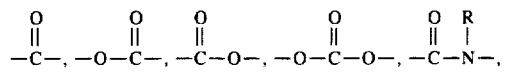

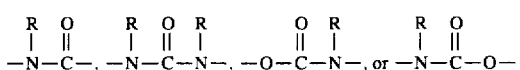

or two $R_1$, $R_3$, $R_4$ or $R_8$ together form a ring.

2. The compound of claim 1, wherein X and Y are each independently —$CH_2$—, —$CH_2CH_2$—, or —$CH(CH_3)$—.

3. The compound of claim 2, wherein X and Y are each —$CH_2$—.

4. The compound of claim 1, wherein $Q_1$ is

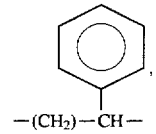

and $R_6$ is H.

5. The compound of claim 1, wherein $R_3$ is H.

6. The compound of claim 1, wherein $Q_2$ is —$CH_2CH_2$—, and $R_1$ is OH.

7. The compound of claim 1, wherein $R_2$ is

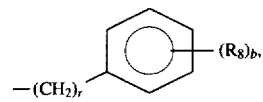

b is 2, and both $R_8$ together form 3,4-methylenedioxy.

8. The compound of claim 1, wherein $R_6$ is H.

9. The compound of claim 1, wherein $R_5$ is —$CH_2C(O)NH_2$.

10. The compound of claim 2, wherein X and Y are each —$CH_2$—, $Q_1$ is

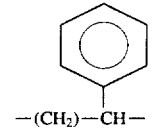

$R_1$ is OH, $R_3$ and $R_6$ are H, and $R_5$ is —$CH_2C(O)NH_2$.

11. The compound of claim 10, wherein $R_2$ is n-pentyl.

12. The compound of claim 10, wherein $R_2$ is

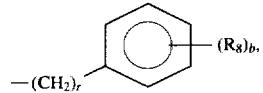

b is 2, and both $R_8$ together form methylenedioxy.

13. The compound of claim 10, wherein $R_2$ is 3,4-dimethoxybenzyl.

* * * * *